(12) United States Patent
Varma

(10) Patent No.: US 8,556,913 B2
(45) Date of Patent: Oct. 15, 2013

(54) METHOD TO ASSIST IN CESAREAN SECTION

(76) Inventor: Rajiv Varma, Shenfield (GB)

( * ) Notice: Subject to any disclaimer, the term of this patent is extended or adjusted under 35 U.S.C. 154(b) by 517 days.

(21) Appl. No.: 12/873,550

(22) Filed: Sep. 1, 2010

(65) Prior Publication Data

US 2010/0324568 A1    Dec. 23, 2010

Related U.S. Application Data

(62) Division of application No. 11/815,807, filed on Aug. 8, 2007.

(30) Foreign Application Priority Data

Feb. 8, 2005   (GB) ............................... 20050002546
Oct. 11, 2005  (WO) ................ PCT/GB2005/003902

(51) Int. Cl.
*A61B 17/42* (2006.01)

(52) U.S. Cl.
USPC .......................................................... 606/122

(58) Field of Classification Search
USPC .................................. 606/119, 121, 122, 124
See application file for complete search history.

(56) References Cited

U.S. PATENT DOCUMENTS

| 713,708 | A |   | 11/1902 | Spire |   |
|---|---|---|---|---|---|
| 3,106,441 | A |   | 10/1963 | Harrison et al. |   |
| 3,480,017 | A | * | 11/1969 | Shute | 606/193 |
| 4,018,230 | A | * | 4/1977 | Ochiai et al. | 606/193 |
| 4,207,891 | A |   | 6/1980 | Bolduc |   |
| 4,338,943 | A | * | 7/1982 | Okamoto et al. | 606/121 |
| 4,480,424 | A |   | 11/1984 | Seldon |   |
| 5,308,327 | A |   | 5/1994 | Heaven et al. |   |
| 6,355,047 | B1 | * | 3/2002 | Wallace et al. | 606/123 |
| 6,648,842 | B2 |   | 11/2003 | Horkel |   |
| 7,018,392 | B2 |   | 3/2006 | Hudson et al. |   |
| 2002/0183779 | A1 |   | 12/2002 | Vigil |   |
| 2004/0059289 | A1 |   | 3/2004 | Garza |   |

FOREIGN PATENT DOCUMENTS

| DE | 10038469 | 2/2002 |
|---|---|---|
| WO | 01/10493 | 2/2001 |

OTHER PUBLICATIONS

Hager et al., Complications of Cesarean Deliveries: Rates and Risk Factors, Feb. 2004, American Journal of Obstetrics and Gynecology, vol. 190, Issue 2, pp. 428-434.

Fasubaa et al., Delivery of the Impacted Head of the Fetus at Cesarean Section After Prolonged Obstructed Labour: A Randomized Comparative Study of Two Methods, Jul. 2002, Journal of Obstetrics and Gynecology, vol. 22, No. 4, pp. 375-378.

(Continued)

*Primary Examiner* — Victor Nguyen
*Assistant Examiner* — Sarah Simpson
(74) *Attorney, Agent, or Firm* — Cheryl F. Cohen

(57) ABSTRACT

A method to allow an easy delivery of a fetus during a Cesarean Section when the fetal head is deeply wedged in the female pelvic cavity using a unique surgical device. The device consists of inflatable portion to lift the fetal head, the inflatable portion being attached to a foldable base plate that can be folded along with the inflatable portion for insertion of the device into the female vagina below the fetal head. The inflatable portion is inflated by injecting a biocompatible fluid with a pressurizing device such as a syringe, pressure bag, hand pump or powered pump. The device may also be utilized in other situations like abdominal delivery of a premature or small baby and when cord prolapse has occurred.

13 Claims, 11 Drawing Sheets

(56) References Cited

OTHER PUBLICATIONS

Landesman et al., Abdominovaginal Delivery: Modification of the Cesarean Section Operation to Facilitate Delivery of the Impacted Head, Mar. 15, 1984, American Journal of Obstetrics and Gynecology, vol. 148, No. 6, pp. 707-710.

Blickstein, Difficult Delivery of the Impacted Fetal Head During Cesarean Section: Interoperative Disengagement Dystocia, 2004, Journal of Perinatal Medicine, vol. 32, No. 6, pp. 465-469.

Arad et al., Vacuum Extraction at Cesarean Section—Neonatal Outcome, 1986, Journal of Perinatal Medicine, vol. 14, No. 2, pp. 137-140.

Bader et al., Maternal and Fetal Catecholamines and Uterine Incision-to-Delivery Interval During Elective Cesarean, Apr. 1990, Obstetrics and Gynecology, vol. 75, No. 4, pp. 600-603.

Khosla et al., Cesarean Section in a Wedged Head, May 2003, Indian Journal of Medical Sciences, vol. 57, No. 5, pp. 187-191.

Ekele, Disengaging Impacted Head at Cesarean Section for Obstructed Labour—Push or Pull?, Jan. 31, 2001, Tropical Doctor, Short Reports, vol. 31, No. 1, pp. 38-39.

Demott et al., The Green Bay Cesarean Section Study II: The Physician Factor as a Determinant of Cesarean Birth Rates for Failed Labor, Jun. 1992, American Journal for Obstetrics and Gynecology, vol. 166, Part 1, pp. 1799-1810.

Murphy et al., Early Maternal and Neonatal Morbidity Associated with Operative Delivery in Second Stage of Labour: A Cohort Study, Oct. 13, 2001, The Lancet, vol. 358, pp. 1203-1207.

\* cited by examiner

METHOD TO ASSIST IN CESAREAN SECTION

CROSS REFERENCE TO RELATED APPLICATIONS

This Present Application is a division of my pending U.S. patent application Ser. No. 11/815,807 (hereinafter, the Parent Application) filed on Aug. 8, 2007 under 35 U.S.C. §371 as the US National State counterpart of PCT International Patent Application Serial No. PCT/GB2005/003902 (hereinafter, the PCT Application) filed on Oct. 11, 2005, which in turn, is the international counterpart of U.K. Patent Application Serial No. GB20050002546 (hereinafter, the U.K. Application) filed on Feb. 8, 2005. The WIPO Publication Number of the PCT Application is WO 2006/085045. This Present Application claims the benefit of and priority to the Parent Application, the PCT Application, and the U.K. Application. The Parent Application is hereby incorporated by reference herein in its entirety thereto.

The Parent Application originally had twenty-five claims. On Feb. 11, 2009, during a telephone interview, the Examiner issued a restriction, designating two groups of claims:
  I. Claims 1-24, drawn to a device for assisting a delivery, classified in class 606, subclass 193.
  II. Claim 25, drawn to a method for dislodging a fetal head, classified in class 606, subclass 122.

At that time, the Applicant provisionally elected Group I without traverse. This was confirmed in the first office action on the merits issued on Feb. 13, 2009. Claim 25 was withdrawn from consideration. This Present Application recites and addresses the invention covered by Group II.

TECHNICAL FIELD OF THE INVENTION

The Present Invention relates to a method of use of a surgical device described herein and in the Parent Application and claimed in the Parent Application, particularly for use in carrying out a Cesarean Section to deliver a baby when vaginal birth is not possible due to various reasons.

BACKGROUND OF THE INVENTION

In last two decades, the incidence of Cesarean Sections (deliveries through abdominal incision) has been constantly rising at a high rate. In the UK and other western countries, the average rate of deliveries by Cesarean Section is around 25% and continues to increase. A significant proportion of Cesarean Sections are performed during the second stage or when women are in late stages of labor. Along with these statistics, there is a rising trend in failed instrumental deliveries, thereby adding to this group of patients. There is evidence that a Cesarean Section performed in these circumstances is prone to higher complications for both the baby and the mother.

The mechanism of difficult delivery of the fetal head during a Cesarean Section is not entirely clear. However, it is clear that such situations rarely, if ever, exist in elective Cesarean Sections. It follows that the impaction of a fetal head is a manifestation of an advanced first stage, and much more likely, an event of the second stage.

Moreover, the impaction seems to be more likely when the second stage is unduly prolonged. A clinician has to decide in these circumstances whether to try an instrumental vaginal delivery or to perform a Cesarean Section. Therefore, some of these cases can exist due to a reluctance to perform an instrumental delivery. The increased use of Cesarean Sections and the reduction in instrumental deliveries has compounded this problem.

There is also an increased use of epidural analgesia in labor, often resulting in a prolonged second stage of labor due to the lack of a maternal urge to push. This could be another reason for impaction of the fetal head in the maternal pelvis.

The deeply engaged fetal head is likely to lead to difficulty in delivery during a Cesarean Section, often leading to a delay in uterine decision—the delivery interval resulting in hypoxic trauma to fetus. The degree of this trauma depends on the length of the delay. There is also a risk of direct injury to the fetus due to force used during the attempted delivery by the operator.

The use of an assistant to help in pushing the fetal head through the vaginal route has been also suggested. This technique can also cause direct trauma to the fetus and lead to delay in delivery. A higher rate of maternal trauma and infections has also been reported while using this technique. Use of the vacuum instrument recommended in this situation, also adds to delay in delivery of an already compromised fetus. Other techniques described are breech extraction, which is often difficult and traumatic unless the operator is familiar with it.

Extension of uterine incision is quite common when the Cesarean Section is carried out at a late stage of labor. An incidence of around 35% has been reported. This often leads to increased blood loss and a need for blood transfusion as well as a higher risk of trauma to the urinary tract during attempts to repair this.

Medicolegal risks of a second stage Cesarean Section are significant. The Royal College of Obstetricians and Gynecologists (U.K.) have suggested that there should be more experienced help at hand when such a situation arises (Sentinel Audit).

To address the above-mentioned problems in childbirth, it would be beneficial to have a device that can be used to assist an obstetrician in delivery of a fetus during a Cesarean Section. Such a device could be of substantial benefit to the patient and could also be used in the situation when a cord prolapse has occurred; thus allowing the fetal head to be pushed up, and thereby allowing more time to prepare for an emergency Cesarean Section.

Such an invention would also be useful when performing Cesarean Sections in premature or small babies, and could be novel when used for dislodging the fetal head, which is deeply wedged in the pelvic cavity, and to deliver fetus without undue delay and trauma that could be beneficial for baby.

Hence, there is clear need for a device, which can dislodge or push the head of the fetus up in the uterus and facilitate delivery in a non-traumatic or safe fashion.

The Present Invention is novel and relates to using such a device to assist surgeon in performing a Cesarean Section.

SUMMARY OF THE INVENTION

The Present Invention comprises a method that uses novel surgical instrument for assisting in a Cesarean Section. It is an advantage of the Present Invention to provide a gentle force to assist the surgeon to dislodge the fetal head that is deeply wedged in the pelvic cavity and to deliver fetus without undue delay and trauma.

The invention relates, in general, to a method for assisting an obstetrician during performance of a Cesarean Section. The method is particularly but not exclusively concerned with supporting and pushing the fetal head up in the pelvis just before a Cesarean Section is attempted. This may be done to dislodge the deeply engaged fetal head and push it in a manner that will assist a surgeon to deliver the baby safely. The method could also be beneficial in other surgical operations.

It is another advantage of the method of the Present Invention to provide the necessary lift for the fetus when an unsuccessful attempt has already been made to deliver the baby vaginally using forceps or vacuum instruments.

Another advantage is to prevent having to deliver the fetal body before delivering the head during a Cesarean Section when the head is impacted or wedged in the pelvis.

Still another advantage of the method of the Present Invention is to reduce the need for an assistant or a surgeon to push the fetus from below when the fetal head is wedged in the pelvic cavity during a Cesarean Section.

Yet another advantage of the method is to prevent trauma to the uterus when delivering the fetus by Cesarean Section in a situation when the fetus is very low in the pelvis.

In order to achieve general aspect of the present invention, the method employs a device comprising an inflatable portion as a main component, which acts as a hydraulic jack to lift the fetal head when it is impacted in the pelvis.

BRIEF DESCRIPTION OF THE DRAWINGS

A complete understanding of the present invention may be obtained by reference to the accompanying drawings, when considered in conjunction with the subsequent detailed description, in which.

DETAILED DESCRIPTION OF PREFERRED EMBODIMENT

The present invention is not limited to the particular shape disclosed. It is expressly understood that a large number of different sizes, shapes and dimensions of both the inflatable portion and plate can be made. The device can also comprise an inflatable portion only, without the need for a separate base plate. The following description is meant to be illustrative only and not limiting. Other embodiments of this invention will be apparent to those of ordinary skill in the art, in view of this description.

Figure 1:
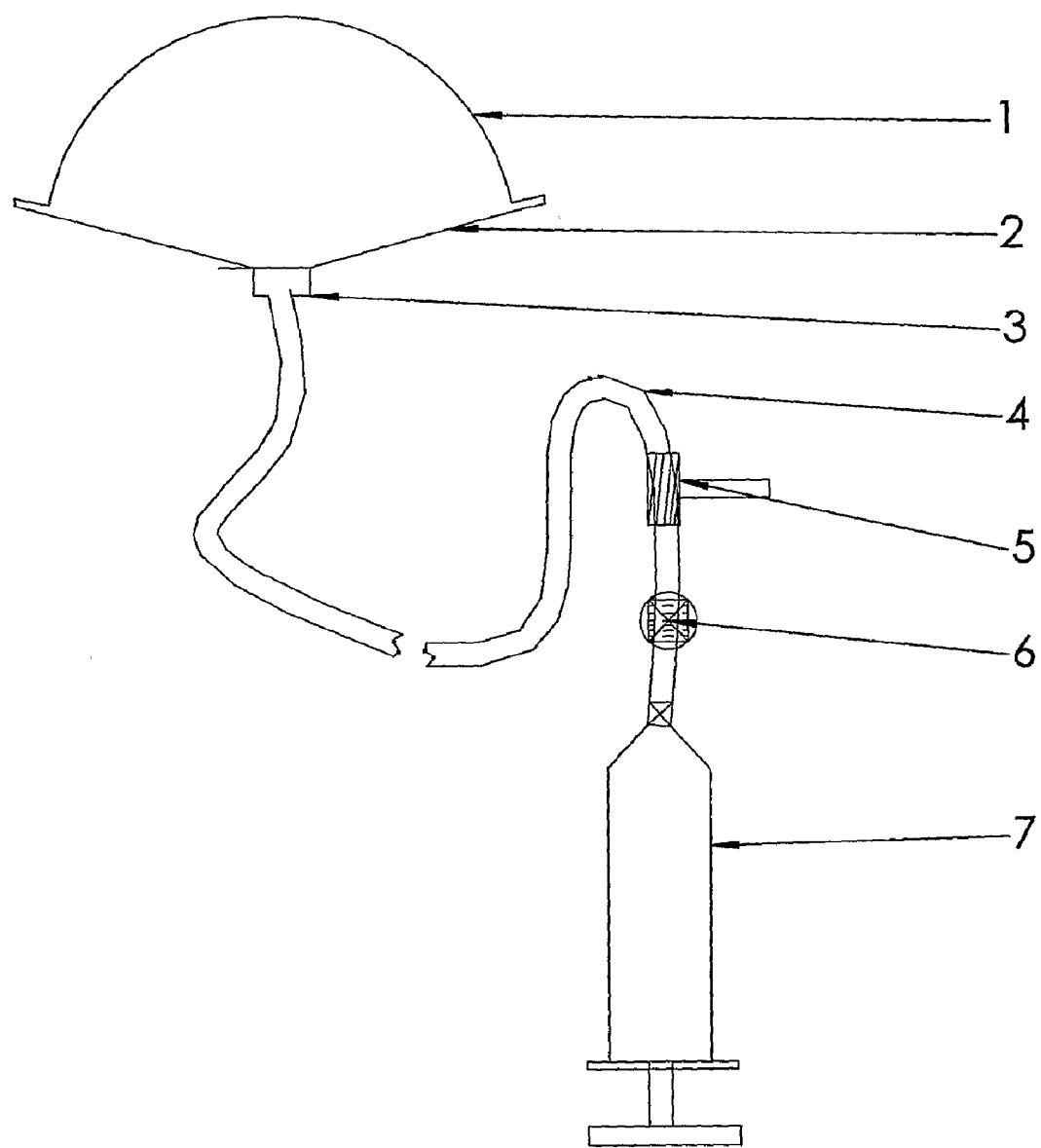
FIG. 1 shows the complete device with the inflated inflatable portion
Figure 5:
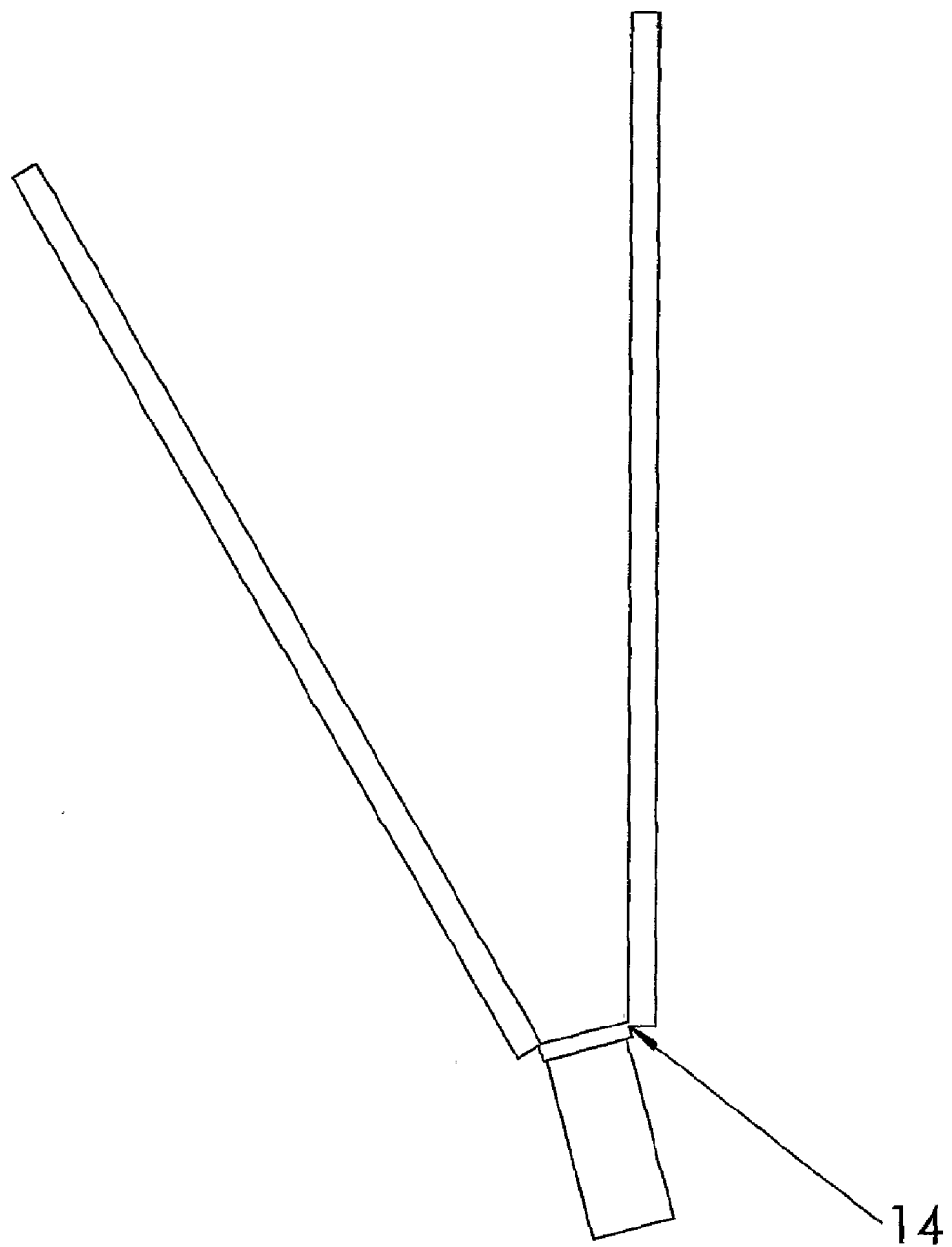
FIG. 5 illustrates a detailed view of the folding mechanism of the base plate.
Figure 6:
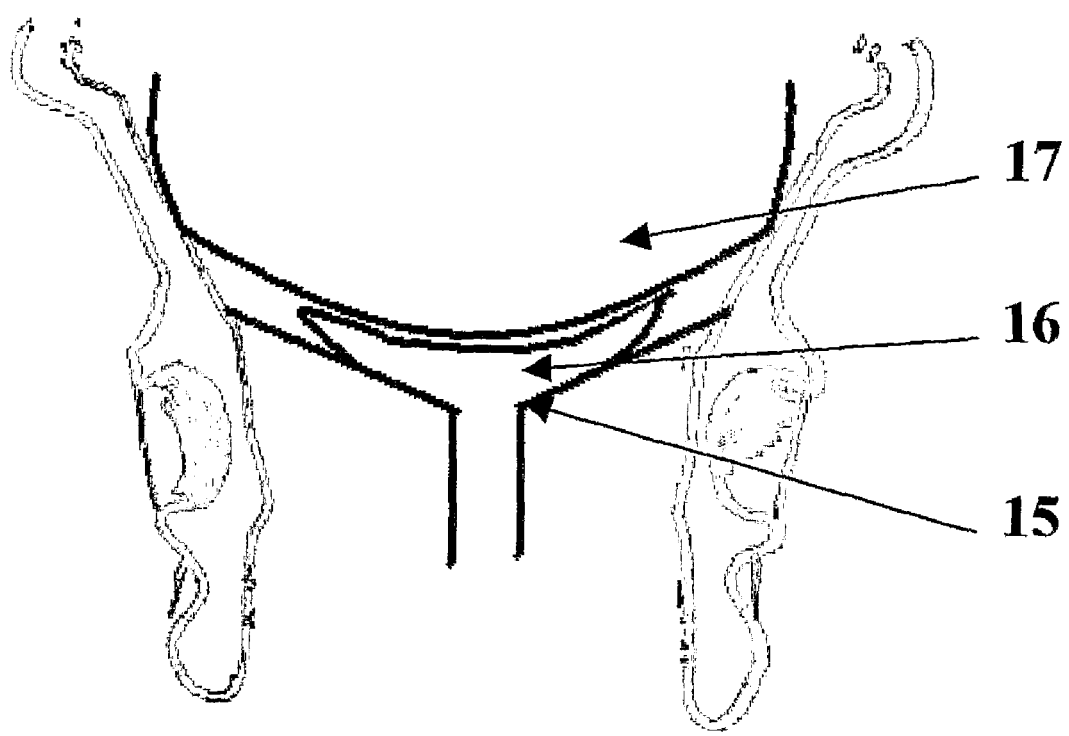
FIG. 6 is a schematic representation of the deflated device inserted below the impacted fetal head.
Figure 7:
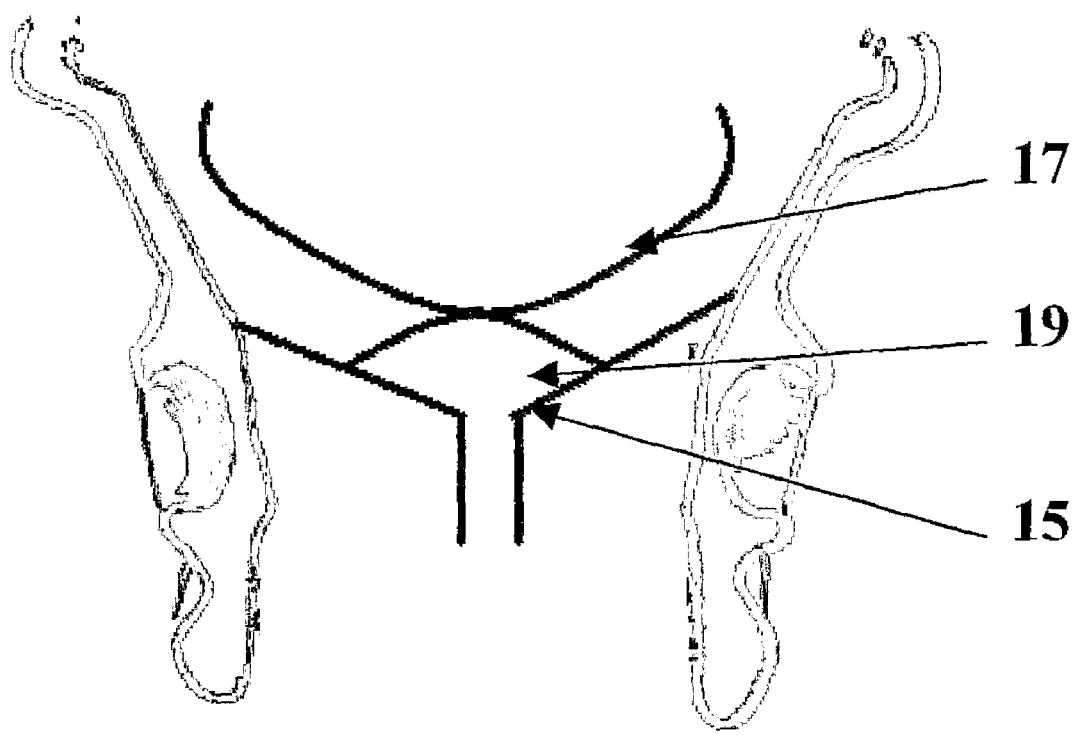
FIG. 7 is a schematic representation of the fully inflated device showing the fetal head disimpacted from the pelvic cavity.
Figure 8:
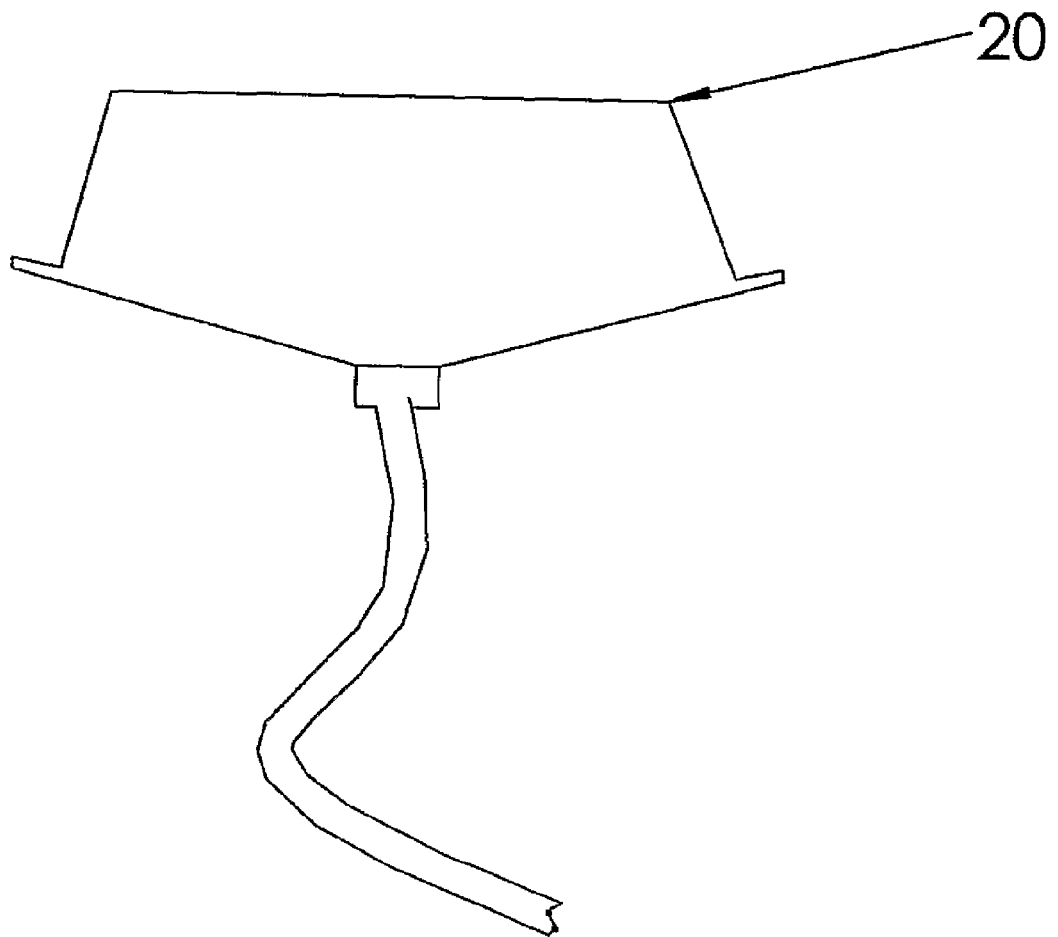
FIG. 8 represents one embodiment of the shape of the inflatable portion
Figure 9:
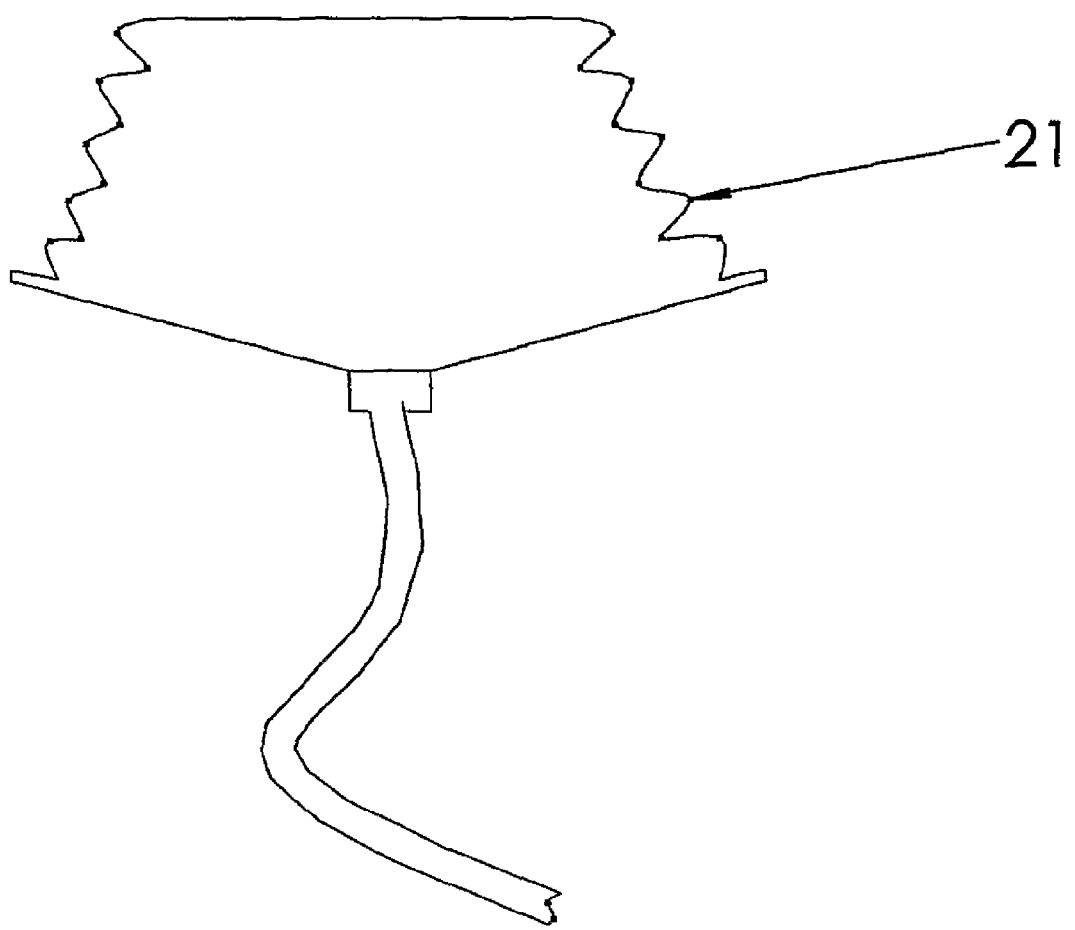
FIG. 9 represents another embodiment of the shape of the inflatable shape
Figure 10:
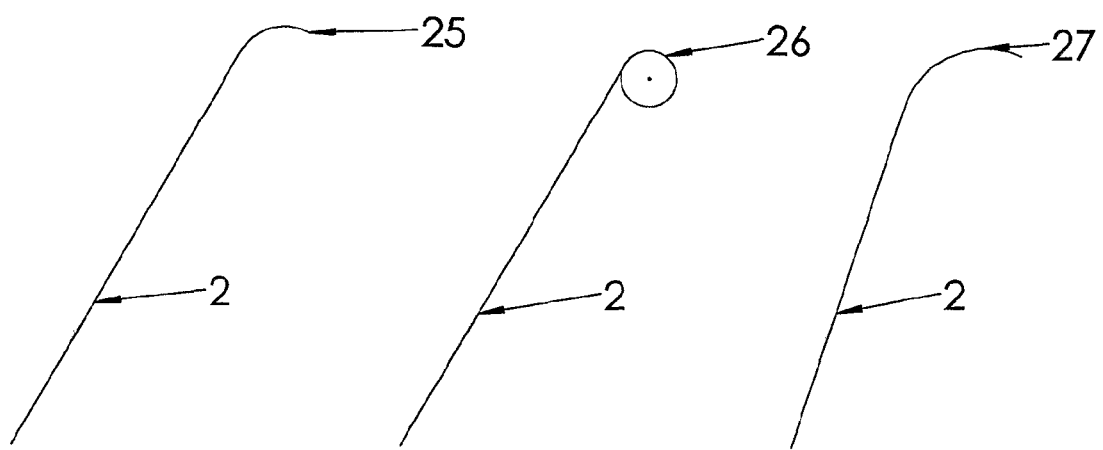
FIG. 10 represents different shapes of edges, which may reduce trauma

The inflatable portion, 1, can be in the shape of a balloon, dome, bellow, square, trapezoid or combination thereof. The inflatable portion is mounted on the plate, 2, by sticking to it by appropriate adhesive, or by mechanical joints, or by heat sealing, or fusing it to the plate, or made as one part or combination thereof. The inflatable portion is integral to the plate, such that the inflatable portion will not unintentionally disconnect from the plate during use. The inflatable portion, 1, can be mounted permanently, semi permanently or temporarily on the plate. The plate, 2, has a hole in the middle to allow the connecting tubing, 4, to be attached to the Inflatable portion for its inflation. The tubing can be attached by using the connector, 3. The base portion of the device is a plate, 2, to which the inflatable portion is attached on the superior surface by any mechanism mentioned above. This plate can be of any size or shape as to allow it to anchor itself to the pelvic floor muscles or ligaments. The plate has to be a firm material, which is biocompatible. The edges, 28, of this plate need to be either soft or rounded to be least traumatic to the maternal tissues. Different shapes of the plate edges are shown in side view in FIG. 10, wherein 25, 26, and 27 represent different atraumatic edge shapes. There are different shapes possible to make the edge. 28, atraumatic. The plate should be able to be folded in at least one direction to allow the device to be squeezed into a smaller size and shape for its insertion into the vaginal below the fetal head. The base plate, 2, also has a simple mechanism, which allows it to be folded in the middle along the short axis. This can be in the form of a thinner area, 14, in FIG. 5, in the plate itself or any other mechanism. As shown in FIG. 1, the base plate, 2, is rigid or semi-rigid plate, and the plate is designed in such a way that the plate can be folded only in one direction towards the superior surface and is fixed in 180 degree angle or flat in the opposite direction. The base plate, 2, also has a simple mechanism, which allows it to be folded in the middle along the short axis; this can be in the form of a thinner area, 4, in the plate itself or any other mechanism. The plate also has edges that are softer or rounded, 28, to make it least traumatic to the maternal tissues when it is inserted into the vagina. The device can be made without the use of base plate as well using any other mechanism, which allows the base of the inflatable portion to fix to the pelvic floor when inflated. The basic principle of using the inflatable portion as a jack to lift the fetal head is the main objective of this invention.

Figure 2:
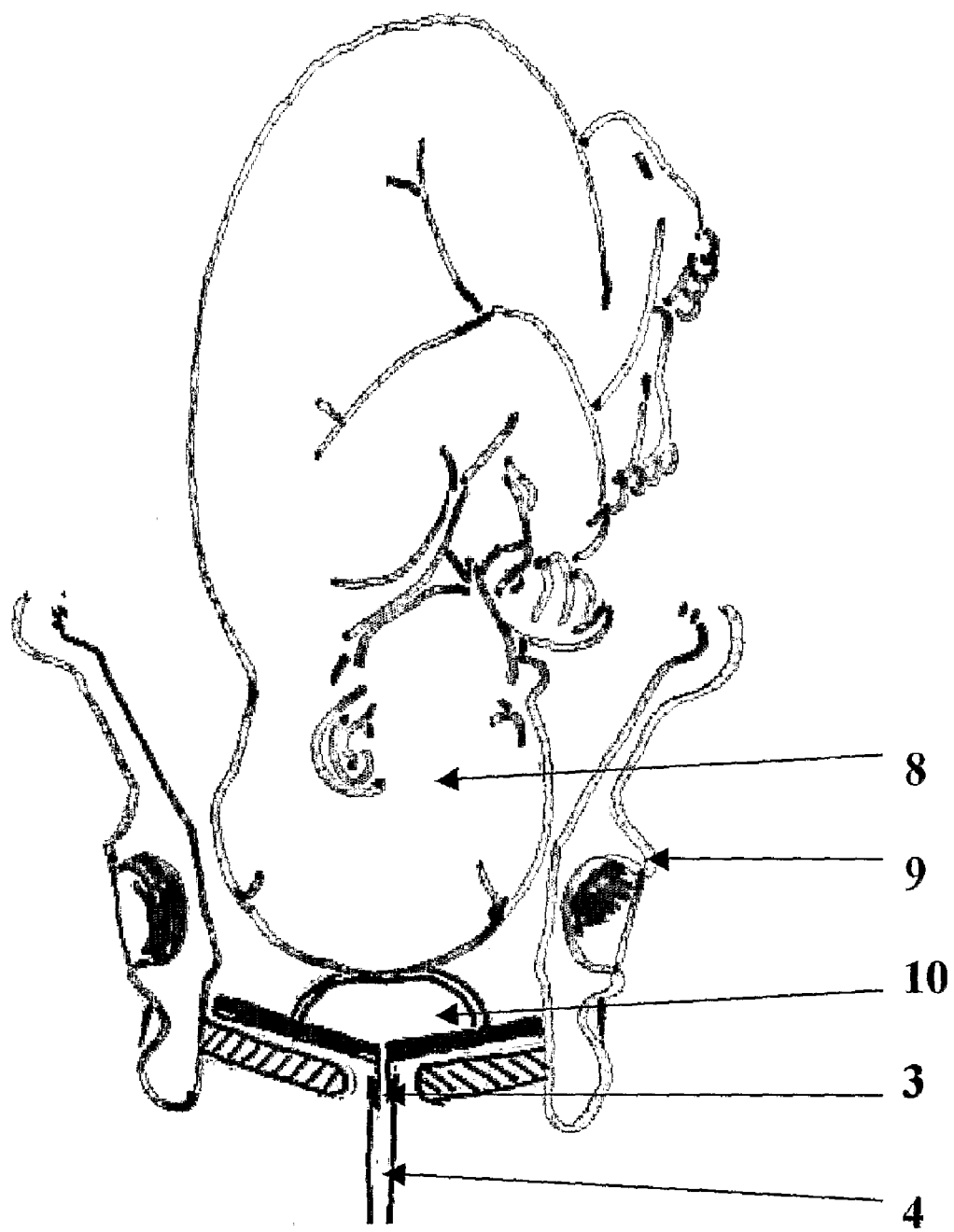
FIG. 2 is a cross section of inflated device placed under the fetal head.
Figure 3:
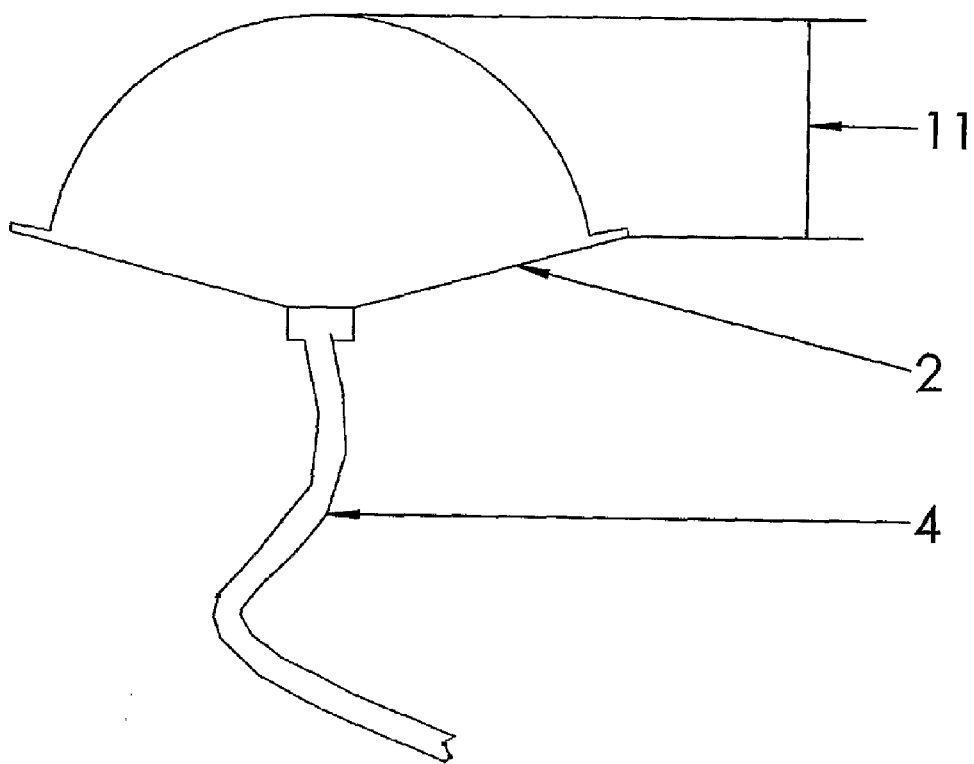
FIG. 3 is an elevation of the complete inflated device taken through the long axis.
Figure 4:
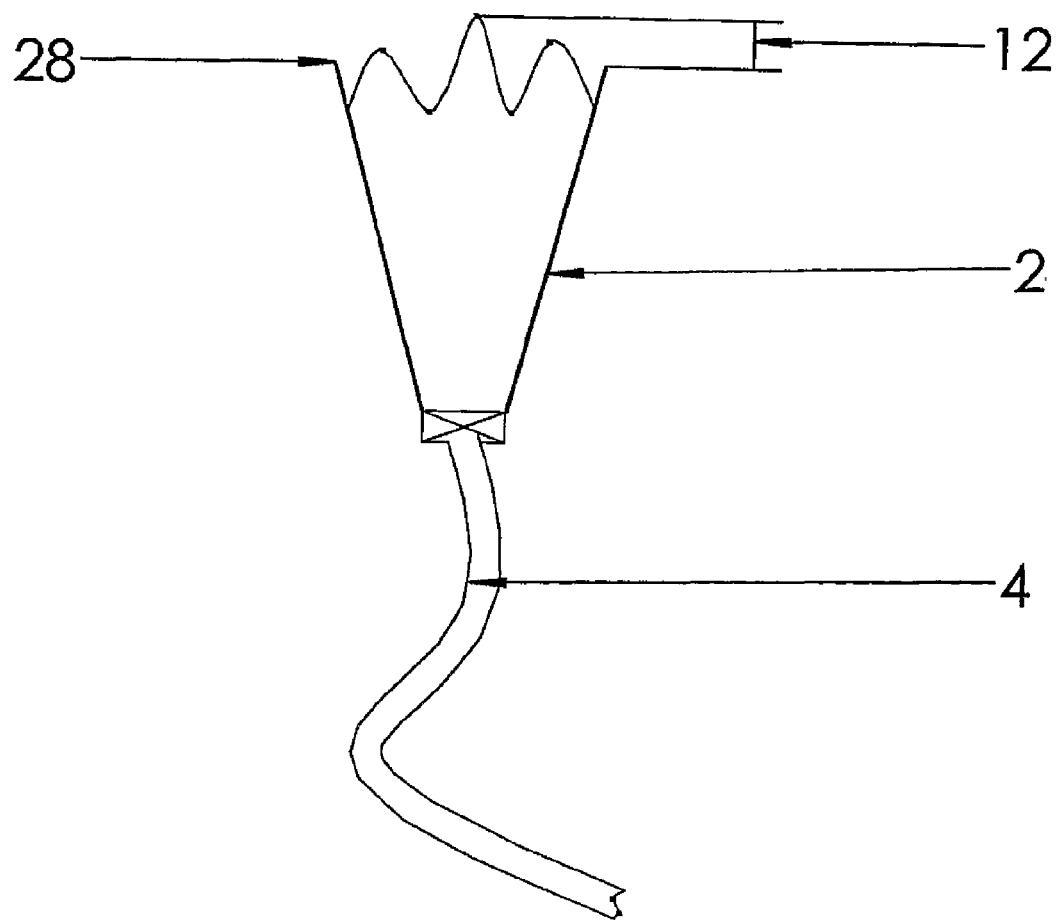
FIG. 4 is an elevation of the complete deflated device taken through the long axis.
Figure 11:
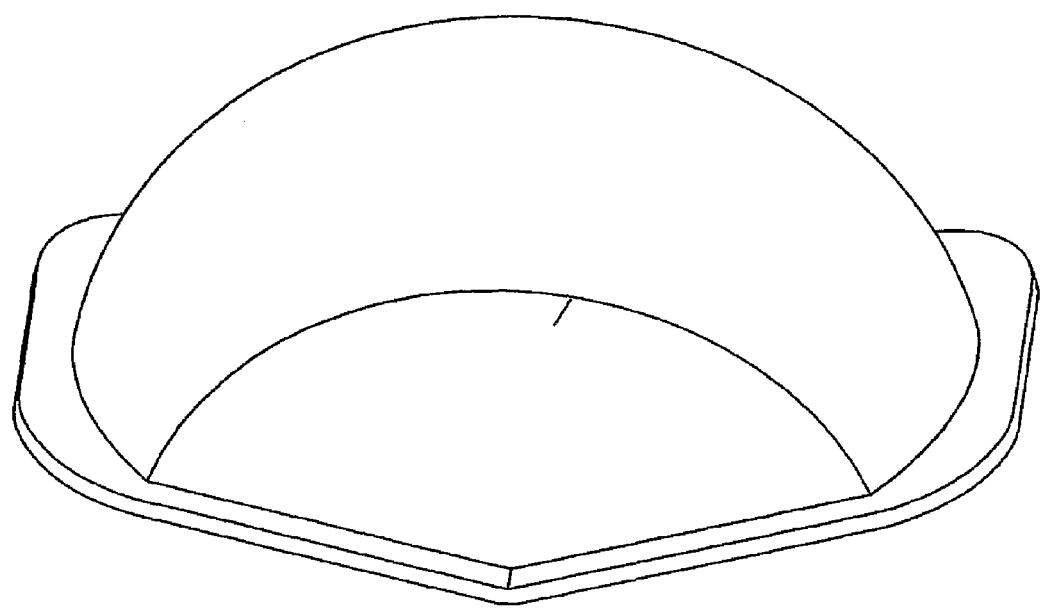
FIG. 11 represents an isometric view of the inflatable portion and plate of the device for better understanding of the invention.

The inflatable portion and plate material should be biocompatible at least to the extent required in all respects. The inflatable material can be elastic or other elastic polymers or it can inelastic like Polyethylene, polyurethane or semi-elastic like silicon. Similarly, the plate material can be rigid like stainless steel, PEEK or ABS or can be not so rigid like PE, PU or rigid silicon. The materials here are examples to provide a better understanding of the invention and do not limit the scope of the invention. As shown in FIG. 1, the inflatable portion of the device is attached to a tube to inject fluid into the inflatable portion. The tube can be an integral part of the inflatable portion of the device or it can be attached separately. The other end of the tube has an appropriate connector to connect the pressurizing mechanism to inject fluid into the inflatable portion. The connector can be a luer connector or an appropriate size rubber tube so that the attachment between the tube and the device is secure and leak proof under the required pressure. The pressure in the balloon can be between 50 mm Hg to 3000 mm Hg. The pressure-relieving valve, 5, is attached in line with the tube, 4, such that the valve opens to relieve extra pressure when set. This is not an essential feature of the device but will be an added safety mechanism. Stopcock, 6, can be opened or closed as desired. The stopcock can be opened to allow the user to push in fluid. The same can be closed to disallow the fluid from flowing out. The stopcock may be a one-way valve. The device is placed in the vagina below the fetal head as shown in FIG. 2. The device is folded in the middle to allow it to place in the vagina as shown in FIG. 4. The tubing, 4, allows the device to be inflated or deflated by the surgeon as required during the surgery. As the device is inflated, the rigid portion of the device, the base plate, 2, takes support along the pelvic floor. FIG. 3 and FIG. 4 represent the principle of operation of this device. When the device is deflated as shown in FIG. 4, the distance, 12, between the edges and top portion of the plate is lesser than the distance, 11, as shown in FIG. 3. This increase in distance pushes the fetal head up. As the inflatable portion is inflated, it helps to straighten up the plate and thereby pushing and fixing the base of the device thereby preventing it from moving in a downward direction. The inflatable portion is then inflated further to push the fetus in appropriate direction. Fluid is injected using a 60 cc syringe, 7. The amount of fluid required is usually around 60-100 cc to elevate the fetal head to 2-3 cm into the pelvic cavity. The fluid may be any biocompatible fluid like saline, glucose solution, ringers lactate or gases like carbon dioxide or such like. Instead of a syringe, any suitable pressurizing device may be used like a pump, blood pressure cuff, pressure balloon, piston cylinder, etc. The device acts like a hydraulic jack normally used in other engineering industries to lift a load or position the load in a proper direction. The movement of the head has to be only minimal to achieve the desired effect of dislodging it from the impacted position. FIG. 11 represents an isometric view of the device for a better understanding of the invention. It shows only the inflatable portion and base plate of the device as the tubing, pressuring member or suck like are self-explanatory.

I claim:

1. A method for dislodging the fetal head wedged deeply in a female pelvic cavity for assisting in delivery of a fetus through abdominal incision, wherein said method comprises:
   a) inserting a surgical device into a female vagina below the fetal head wherein said device comprises:
      an inflatable portion acting as a hydraulic jack to lift the fetal head;
      a foldable base plate having an aperture at the center region wherein said base plate is attached to said inflatable portion forming a leak proof seal therebetween for receiving a fluid therein; the plate being bendable only along at least one thinner area in response to a change in pressure within the device;
      a tubing section, having two ends, attached to said inflatable portion for injecting fluid into said inflatable portion at one end; and
      a pressurizing device attached at the other end of the tubing section;
   b) inflating said inflatable portion by injecting fluid or gas through said tubing section by means of the pressurizing device, and fixing said base plate along the pelvic floor to prevent the base plate from moving in a downward direction toward the vaginal opening;
   c) pushing the fetal head in an upward direction, away from the vaginal opening, by further inflating said inflatable portion; and
   d) surgically incising the female abdomen to expose the fetus, and reaching between said inflated inflatable portion and the fetal head to extract the head of the fetus before the body.

2. The method of claim 1, further comprising folding or compressing said base plate for ease of insertion into the female vagina prior to inflating said inflatable portion.

3. The method of claim 2 wherein said base plate elastically unfolds or expands to prevent it from moving in a downward direction toward the vaginal opening.

4. The method of claim 1 wherein said pressurizing device is a syringe, hand pump, pressure bag, or powered pump.

5. The method of claim 1 further comprising controlling the degree of inflation of said inflatable portion using said pressuring device.

6. The method of claim 1 further comprising controlling the degree of inflation of said inflatable portion using a pressure relieving valve inserted into the path of the fluid or gas.

7. The method of claim 6 wherein the pressure relieving valve is a stopcock.

8. The method of claim 1 further comprising deflating said inflatable portion after extraction of the fetus, and thereafter removing the surgical device through the vagina.

9. The method of claim 1 further comprising using the surgical device for abdominal delivery of a premature baby.

10. The method of claim 1 further comprising using the surgical device for delivery of a baby in cord prolapsed.

11. The method of claim 1 further comprising using the surgical device for delivery of a baby in pre-term labor.

12. The method of claim 1, wherein the plate is permanently attached to the inflatable portion only about its perimeter by a bond taken from the group consisting of adhesive, mechanical joint, heat seal, and fusion.

13. The method of claim 1, wherein the plate is bendable only substantially in a centered region.

* * * * *